US012693361B2

(12) United States Patent
Li et al.

(10) Patent No.: US 12,693,361 B2
(45) Date of Patent: Jul. 28, 2026

(54) T1rho DISPERSION CHARACTERIZATION BY MAGNETIC RESONANCE FINGERPRINTING

(71) Applicant: The Cleveland Clinic Foundation, Cleveland, OH (US)

(72) Inventors: Xiaojuan Li, Cleveland, OH (US); Brendan Eck, Cleveland, OH (US); Jeehun Kim, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 140 days.

(21) Appl. No.: 18/667,174

(22) Filed: May 17, 2024

(65) Prior Publication Data

US 2024/0385269 A1 Nov. 21, 2024

Related U.S. Application Data

(60) Provisional application No. 63/467,792, filed on May 19, 2023.

(51) Int. Cl.
*G01R 33/50* (2006.01)
*A61B 5/00* (2006.01)
*G01R 33/56* (2006.01)

(52) U.S. Cl.
CPC .............. *G01R 33/50* (2013.01); *A61B 5/004* (2013.01); *G01R 33/5608* (2013.01)

(58) Field of Classification Search
CPC ...... G01R 33/5608; G01R 33/50; A61B 5/004
See application file for complete search history.

(56) References Cited

U.S. PATENT DOCUMENTS 9,974,490 B2 * 5/2018 Bachschmidt ..... G01R 33/5608
10,459,055 B2 * 10/2019 Griswold ........... G01R 33/4835

FOREIGN PATENT DOCUMENTS

CN 111685764 A * 9/2020 ............... A61B 5/72

OTHER PUBLICATIONS

Machine Translation of CN 111685764 A (Year: 2020).*
International Search Report and Written Opinion for PCT/US2024/029844 dated Sep. 6, 2024, 17 pages.
Velasco Carlos, et al. "Simultaneous T1, T2, and T1 [rho] cardiac magnetic resonance fingerprinting for contrast agent free mocardial tissue characterization". Magnetic Resonance in Medicine. vol. 87, No. 4. Nov. 19, 2021, pp. 1992-2002.

(Continued)

*Primary Examiner* — Gregory H Curran
(74) *Attorney, Agent, or Firm* — McDonald Hopkins LLC

(57) ABSTRACT

Magnetic resonance fingerprinting (MRF) is used to quantify $T_{1\rho}$ dispersion across spin-lock frequencies and enables simultaneous mapping of $T_1$, $T_2$, and $T_{1\rho}$ dispersion. $T_{1\rho}$ at a specific FSL may be determined by retrospectively computation based on the results of the $T_{1\rho}$ dispersion MRF dictionary and pattern matching results. The $T_{1\rho}$ dispersion characteristic may be used to identify and track tissue parameters (such as osteoarthritis and muscle degeneration) before being expressed in other measurable manners.

20 Claims, 5 Drawing Sheets

100

(56) References Cited

OTHER PUBLICATIONS

Thomas James Fletcher, et al. "Dictionary Generation and Matching with Conditional Invertible Neural Networks for Cardiac MR Fingerpinting", Proceedings of the Joint Annual Meeting ISMRM-ESMRMB 2022 & ISMRT Annual Meeting, London, UK, 07-12, May 2022, ISMRM, 2030 Addison Street, 7th floor Berkely CA 94704. vol. 30, 1760, Apr. 22, 2022.

Adelnia Fatemeh, et al. "Tissue characterization using R1rho dispersion imaging at low locking fields", Magnetic Resonance Imaging, vol. 84, May 28, 2021, pp. 1-11, XP093192980, Tarrytown, NY, US.

Qi Peng and Can Wu. "Fast 3D T1rho Dispersion MRI with Interleaved Phase Cycling MAPSS", Proceedings of the Joint Annual Meeting ISMRM-ESMRMB 2022 & ISMRT Annual Meeting, London, UK, 07-12, May 2022, 2030 Addison Street, 7th floor Berkely CA 94704. No. 4064, Apr. 22, 2022.

* cited by examiner

100

| Execute MRF protocol | 110 |

| Generate fingerprints | 120 |

| Generate dictionary based on T1ρ model | 130 |

| Compare and match generated fingerprints with fingerprints in the generated dictionary | 140 |

| Identify T1ρ, T1ρ dispersion, and other parameters of interest | 150 |

| Identify tissue Properties | 160 |

T1rho DISPERSION CHARACTERIZATION BY MAGNETIC RESONANCE FINGERPRINTING

CROSS-REFERENCE TO RELATED APPLICATIONS

This application claims the benefit of U.S. provisional application Ser. No. 63/467,792 filed May 19, 2023, the entire contents of which are incorporated by reference.

STATEMENT OF GOVERNMENT-SPONSORED RESEARCH

This invention was made with government support under AG070321 and AR007505 awarded by the National Institutes of Health. The government has certain rights in the invention.

BACKGROUND

The value of medical imaging research has grown significantly in recent decades. Techniques such as magnetic resonance fingerprinting (MRF), functional magnetic resonance imaging (fMRI), magnetic resonance spectroscopy (MRS), diffusion tensor imaging (DTI), and positron emission tomography (PET) provide a non-invasive method of exploring the structure and function of tissues within the body. These advanced imaging techniques have played a crucial role in advancing many fundamental areas of medical science, including the study of cancer, multiple sclerosis, soft tissue injuries, joint or spinal injuries, Parkinson's disease, Alzheimer's disease, and other conditions.

In particular, MRF is characterized by a pseudo-randomized acquisition strategy, pattern matching, and tissue property visualization. MRF is a flexible, rapid imaging technique that can allow simultaneous quantification of multiple tissue properties. Generally MRF involves generating an MRI pulse sequence by varying various MR acquisition parameters. Data acquired from these pulse sequences represent "fingerprints" that are different for different tissues/tissue properties. These fingerprints (e.g., from each pixel or voxel of the acquired data) can then be pattern matched to a dictionary of known fingerprints to identify the type of tissue and/or its properties.

BRIEF SUMMARY OF THE INVENTION

According to a first example of the present disclosure, a magnetic resonance fingerprinting (MRF) method comprises: applying an MRF pulse sequence to tissue of a subject; acquiring magnetic resonance (MR) signal data as a result of the application of the MRF pulse sequence; comparing the MR signal data to a predefined MRF dictionary, the MRF dictionary comprising a model of $T_{1\rho}$ dispersion; and determining a property of the tissue from the $T_{1\rho}$ dispersion model based on a result of the comparison.

In various embodiments of the above disclosure, $T_{1\rho}$ dispersion is modeled according to:

$$T_{1\rho}(\omega) = \frac{\left(q^2 D\right)^2 + \omega^2}{\gamma^2 g^2 D} = m^2\left(q^2 D\right)^2 + m^2 \omega^2$$

where $$T_{1\rho}(0) = m^2\left(q^2 D\right)^2 = T_2 \text{ and } T_{1\rho}(\omega) = T_2 + (m\omega)^2$$

where $\gamma$ is a hydrogen gyromagnetic ratio, D is a self-diffusion coefficient, q is a spatial frequency of a local magnetic field variation, g is a mean local magnetic gradient strength, $\omega$ is frequency, and m is a mediation coefficient that mediates a strength of a $T_{1\rho}$ dispersion effect and represents a combination of $\gamma$, D, and g; wherein $T_{1\rho}$ dispersion is modeled according to:

$$T_{1\rho}(\omega) = T_2 + m\omega$$

where $\omega$ is frequency, and m is a mediation coefficient that mediates a strength of a $T_{1\rho}$ dispersion effect and represents a combination of a hydrogen gyromagnetic ratio, a self-diffusion coefficient, and a mean local magnetic gradient strength; the determined tissue property relates to tissue degeneration; the method further comprises: identifying an osteoarthritis or muscle degeneration condition in the subject based on the identified property; the method further comprises: applying a plurality MRF pulse sequencies, and tracking a change in $T_{1\rho}$ dispersion of the tissue of the subject over the plurality of applied MRF sequences; the method further comprises: applying a plurality MRF pulse sequencies, and tracking a change in the determined tissue property over the plurality of applied MRF sequences; the MRF pulse sequence includes a single fixed spin-lock frequency; the method further comprises: determining a $T_{1\rho}$ dispersion by retrospectively determining $T_{1\rho}$ at a plurality of spin-lock frequencies based on the model of the MRF dictionary; the MRF dictionary comprises fingerprints of at least $T_1$, $T_2$, and m; and/or the MR signal data is compared to the predefined MRF dictionary with a machine learning system trained to identify MR properties of the MRF dictionary based on input MR signal data.

DETAILED DESCRIPTION OF THE DRAWING

Figure 1:
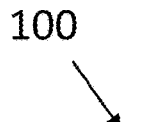
FIG. 1 illustrates an example method for characterizing $T_{1\rho}$ dispersion in accordance with the present disclosure.

Considering the above, the present disclosure relates to a data acquisition and reconstruction framework, and more particularly, a framework to enable $T_{1\rho}$ dispersion magnetic resonance fingerprinting (MRF) data acquisition and reconstruction.

In magnetic resonance imaging, an MRI pulse sequence is a particular setting of radiofrequency excitation pulses and field gradient waveforms timed in a manner that yields a particular image appearance. A multiparametric MRI is a combination of two or more sequences, and/or includes other specialized MRI configurations such as spectroscopy. A pulse sequence is generally defined by multiple parameters including time to echo (TE), time to repetition (TR), flip angle, field of view and matrix size, inversion pulses, spoiler gradients, echo train length (ETL), special acquisition of k-space, post contrast imagine, and diffusion weighting. These pulse sequences can be broadly grouped into either a spin echo sequence, an inversion recovery sequence, a gradient echo sequence, a diffusion weighted sequence, saturation recovery sequences, echo-planar pulse sequences, and spiral pulse sequences. Multiple sequences are used evaluate a tissue, and the combination of sequences is referred to as an MRI protocol.

Commonly, tissues are characterized by relaxation times $T_1$ and $T_2$. $T_1$ is the time constant that determines the rate at which excited protons return to equilibrium. $T_1$ is a measure of the time taken for spinning protons to realign with an external magnetic field. $T_2$ is the time constant that determines the rate at which the excited protons reach equilibrium and is a measure of the time taken for spinning protons to lose phase coherence among the nuclei spinning perpendicular to the main magnetic field.

The most common MRI sequences are $T_1$-weighted and $T_2$-weighted scans. $T_1$-weighted scans use short TE and TR times, while $T_2$-weighted scans use longer TE and TR times. In $T_1$-weighted images, the contrast and brightness are determined by $T_1$ properties of the tissues, while in $T_2$-weighted images, the contrast and brightness are determined by $T_2$ properties.

A less common MRI sequence includes $T_{1\rho}$. $T_{1\rho}$ is a potential biomarker of musculoskeletal diseases such as osteoarthritis and muscle degeneration. $T_{1\rho}$ has elements of both $T_1$ and $T_2$ weighting, and is dependent on the $T_1$ and $T_2$ of the tissue, but can additionally select for different properties within the tissue. The relaxation time of $T_{1\rho}$ is a tissue property that can be probed in order to assess tissue composition (e.g., glycosaminoglycan content in cartilage and fiber type proportion in skeletal muscle). $T_{1\rho}$ characterizes longitudinal relaxation during the application of a "spin-locking" radiofrequency excitation magnetic $(B_1)$ pulse. $T_{1\rho}$ is influenced by interactions of large biomolecules and water, and is dependent on the spin-lock frequency (FSL) of the applied $B_1$ field. And the dispersion of $T_{1\rho}$ across FSL values is an additional magnetic property beyond single-frequency $T_{1\rho}$ that is sensitive to chemical exchange and diffusion or diffusive exchange.

$T_{1\rho}$ relaxation can be quantified via multiple spin-lock magnetization preparation pulses at a given FSL with varied spin-lock times (TSL) to acquire $T_{1\rho}$ weighted images. Typically, curve-fitting of $T_{1\rho}$ weighted images is performed using an exponential decay equation. By quantifying $T_{1\rho}$ at multiple FSL values, the $T_{1\rho}$ dispersion of a tissue can be characterized.

$T_{1\rho}$ dispersion represents a relatively new approach to MRI tissue characterization. Advantageously, $T_{1\rho}$ dispersion is thought to allow for higher sensitivity and specificity when analyzing some particular tissues and tissue properties compared to traditional $T_1$ and $T_2$. With $T_{1\rho}$ dispersion, the $T_{1\rho}$ signal across FSL from tissues is amplified which increases the sensitivity and therefore ability to detect macromolecular components in tissue. Indeed, disease processes may be detected based on large molecules directly rather than indirectly through their effects on water, as in $T_1$ and $T_2$ imaging.

Additionally, $T_{1\rho}$ dispersion can be monitored for a single patient over a period of time to track changes a patient's tissue properties. Thus, dispersion may allow for earlier detection of tissue degeneration, musculoskeletal changes, and other tissue-related changes that could be used to assess and diagnose various diseases. These MRF properties may be related to particular tissue properties via normative databases (e.g., collections of related properties among large populations), or via pattern recognition techniques such as those utilizing machine learning systems.

Monitoring $T_{1\rho}$ and $T_{1\rho}$ dispersion using traditional MR techniques can be prohibitively time consuming as they generally would require multiple scans at different FSL. They can also require prohibitively high energy deposition rates at relatively high FSL values. These factors can be barriers in acquiring $T_{1\rho}$ information. However, the use of magnetic resonance fingerprinting (MRF) methods can be utilized to reduce scan times and high energy deposition. Utilizing MRF in this way allows for the measurement of multiple tissue properties in a single acquisition because each tissue type has a unique signal response to a given input sequences which depends on its physical, chemical, and biological properties. Further $T_{1\rho}$ can be determined from a scan at a single, fixed FSL, and $T_{1\rho}$ dispersion MRF can yield $T_{1\rho}$ maps at a single FSL retrospectively.

The embodiments described herein serve to improve conventional MRF by providing a framework to enable $T_{1\rho}$ dispersion MRF data acquisition and reconstruction. According to the present disclosure, $T_1$, $T_2$, and $T_{1\rho}$ can be simultaneously mapped, and MRF can be used to quantify $T_{1\rho}$ at a single spin-lock frequency. According to the techniques of the present disclosure, maps of $T_1$, $T_2$, and $T_{1\rho}$ dispersion can be generated. Those maps can then be used to retrospectively create $T_{1\rho}$ relaxation time maps without having to measure $T_{1\rho}$ at each FSL.

Turning to the figures, FIG. 1 illustrates a flowchart of an example method 100 according to the present disclosure. As with other implementations of MRF, the method begins by executing an MRF protocol 110, or a series of pulse sequences, and acquiring associated MR signal data or fingerprints 120 in response. Here, the executed MRF protocol scan parameters include FSL, flip angle, repetition time, and echo time, which may be varied or fixed. In one example embodiment, the FSL is fixed, and the $T_{1\rho}$ mapping can be made retrospectively for other (non-scanned) FSL.

As noted above, the fingerprints from the application of the MRF protocol 110 are then compared to and matched with a collection of simulated fingerprints in a generated dictionary 130 of expected signal patterns. In some embodiments, this comparison may be performed by pattern matching techniques, such as with machine learning systems. In some embodiments, the comparison may be performed with look-up tables or the like. If an exact match is not found in such a table, a closest match may be selected or parameters may be determined by interpolation or similar techniques between two or more closest matches.

The generated dictionary 130 models $T_{1\rho}$ dispersive effects across FSL, and can relate $T_{1\rho}$, FSL, hydrogen gyromagnetic ratio, self-diffusion coefficient, spatial frequency of a local magnetic field variation, and related mean gradient strength. The $T_{1\rho}$ dispersion MRF method uses variable FSL, variable flip angle, fixed repetition time, and fixed echo time in this implementation, but is not restricted to fixed repetition time or fixed echo time. Depending on the embodiment, various models may be used to determine/model the value of $T_{1\rho}$. According to one example, the dictionary models $T_{1\rho}$ dispersion by the following:

$$T_{1\rho}(\omega) = \frac{\left(q^2 D\right)^2 + \omega^2}{\gamma^2 g^2 D} = m^2\left(q^2 D\right)^2 + m^2 \omega^2 \qquad \text{(Equation 1)}$$

where $$T_{1\rho}(0) = m^2\left(q^2 D\right)^2 = T_2 \text{ and } T_{1\rho}(\omega) = T_2 + (m\omega)^2 \qquad \text{(Equation 2)}$$

Equations (1) and (2) above relate $T_{1\rho}$, FSL($\omega$), hydrogen gyromagnetic ratio ($\gamma$), self-diffusion coefficient (D), spatial frequency of a local magnetic field variation (q), related mean gradient strength (g), and a mediation coefficient (m) that mediates the strength of a $T_{1\rho}$ dispersion effect and represents a combination of $\gamma$, D, and g. A larger value of m represents a greater dispersion, and a zero value represents no dispersion. The quantities $g^2 D$ and $q^2 D$ are related to $T_2$ by the following:

$$T_2 = \frac{\left(q^2 D\right)^2}{\gamma^2 g^2 D} \qquad \text{(Equation 3)}$$

$$m^2 = \frac{1}{\gamma^2 g^2 D} \qquad \text{(Equation 4)}$$

at FSL=0 and $T_{1\rho}=T_2$.

In other embodiments, $T_{1\rho}$ may be modeled with a linear dispersion model such as:

$$T_{1\rho}(\omega) = T_2 + m\omega \qquad \text{(Equation 5)}$$

After the MRF dictionary models $T_{1\rho}$ dispersion using the above formulae, dictionary generation proceeds as before, but with $T_{1\rho}$ relaxation being dependent on FSL. $T_1$, $T_2$, $T_{1\rho}$ dispersion, and with m being directly mapped instead of $T_1$, $T_2$, and $T_{1\rho}$. A single FSL still leads to $T_{1\rho}$ mapping, and MRF without $T_{1\rho}$ mapping results in m=0. Data acquisition is carried out as in existing $T_{1\rho}$ MRF methods, but with varied FSL.

The dictionary is generated to contain three parameters that characterize the relevant magnetic characteristics of a tissue—namely, $T_1$, $T_2$, and m. After acquisition of $T_{1\rho}$ dispersion MRF data, a 3D spatial total variation-regularized, temporal low rank reconstruction can be employed to suppress noise and undersampling artifacts and obtain tissue property maps.

The fingerprints are then compared to and matched with 140 the collection of fingerprints in the generated dictionary. As a result, $T_1$, $T_2$, $T_{1\rho}$ dispersion, and m are all directly mapped instead of just $T_1$, $T_2$, and $T_{1\rho}$. Once fingerprints are matched 140, the properties of interest (such as $T_{1\rho}$) may be identified 150. As noted above, this MRF property may be related to tissue properties based on normative databases or like techniques, and may be monitored over a period of time to identify and/or track disease progression.

The above technique has been verified using at least two phantoms. In one example, a digital cylindrical phantom with known ground truth $T_1$, $T_2$, and $T_{1\rho}$ dispersion values was used for in silico implementation of the $T_{1\rho}$ dispersion MRF sequence. Particularly, a 500 frame MRF sequence was used with the acceleration factor R=60 and a matrix size of 192×192×16.

In another example, an agarose gel phantom with glucose addition was used to assess $T_{1\rho}$ dispersion using $T_{1\rho}$ dispersion MRF as compared to a reference method. During validation, the MRF sequence utilized a 15-channel Tx/Rx knee coil, while the reference method was a $T_2/T_{1\rho}$ magnetization-prepared angle-modulated partitioned k-space spoiled gradient echo snapshots (MAPSS) at a matrix size of 192×192×16 with $T_{1\rho}$ quantifications at FSL=50, 100, 200, and 500 Hz. Four echoes were acquired for each FSL, with TSL=0, 10, 30, and 70 ms. A total scan time was 10 minutes. The aforementioned $T_{1\rho}$ dispersion model was fitted to MAPSS $T_{1\rho}$ values for comparison with MRF. $T_{1\rho}$ MRF used the same sequence settings as in simulation but with a matrix size 96×96×16 and a 2.5 minute scan time.

Figure 2:
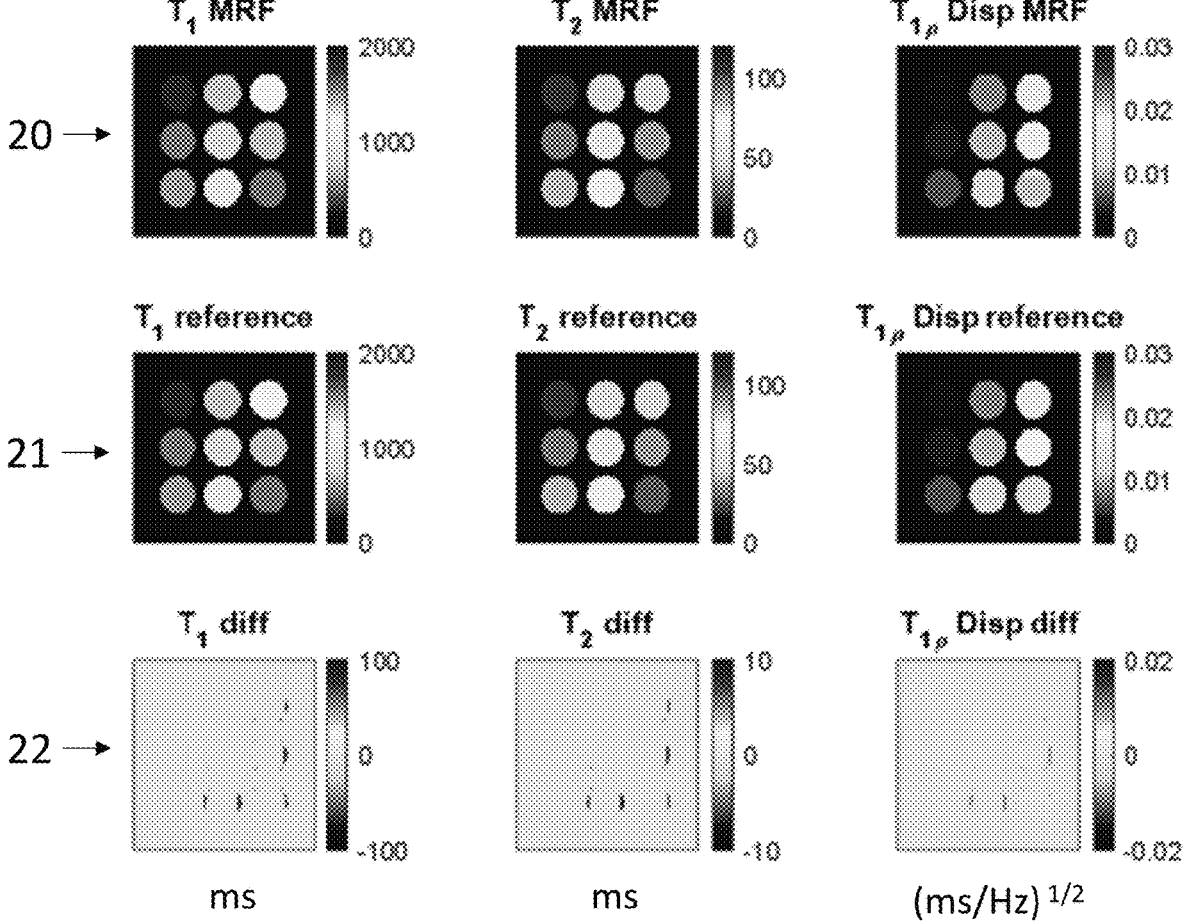
FIG. 2 illustrates $T_1$, $T_2$, and $T_{1\rho}$ dispersion from MRF as compared to a ground truth reference.

FIGS. 2-5 illustrate the results of these simulations. In particular, FIG. 2 illustrates $T_1$, $T_2$, and $T_{1\rho}$ dispersion from MRF 20 as compared to a ground truth reference 21. As illustrated, by comparing the respective maps of each of $T_1$, $T_2$, and $T_{1\rho}$ generated by MRF 20 to those generated by the ground truth reference 21, the difference between $T_{1\rho}$ dispersion MRF and $T_{1\rho}$ dispersion reference is minimal compared to the differences between $T_1$ and $T_2$ and their respective ground truth references. This difference is visually illustrated in map sequence 22.

Figure 3:
FIG. 3 illustrates $T_{1\rho}$ relaxation time maps retrospectively generated at spin-lock frequencies (FSL) of FSL=50, 100, 200, and 500 Hz from MRF as compared to ground truth generated maps.

FIG. 3 illustrates $T_{1\rho}$ dispersion maps 30 retrospectively generated at FSL=50, 100, 200, and 500 Hz from MRF as compared to ground truth generated maps 31. Again, comparison between the MRF maps 30 and the maps generated via the reference technique are extremely similar at each FSL.

Figure 4:
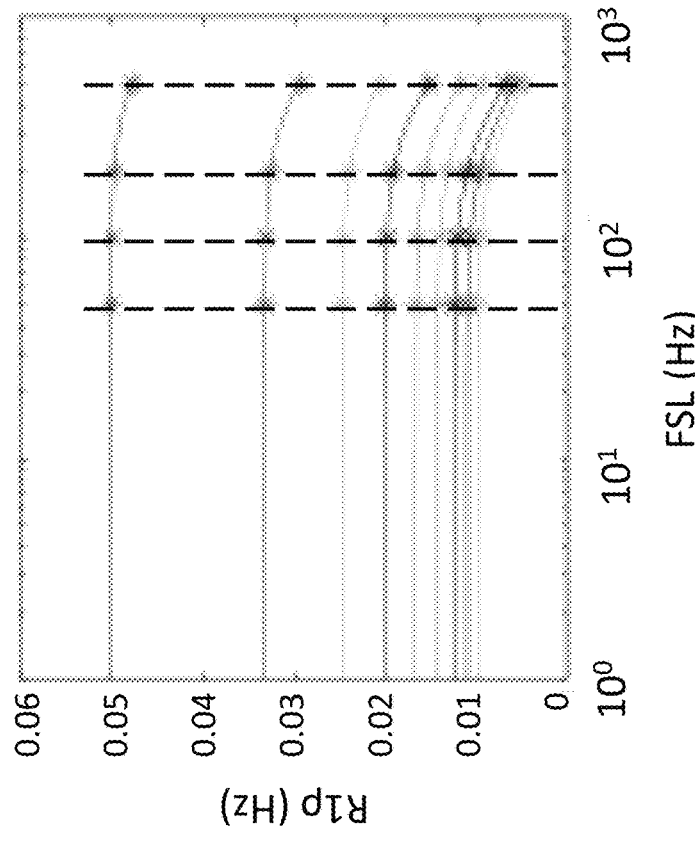
FIG. 4 illustrates measured $T_{1\rho}$ and $R_{1\rho}$ in ROIs of the retrospectively MRF-derived maps as compared to the ground truth dispersion curve.
Figure 4:
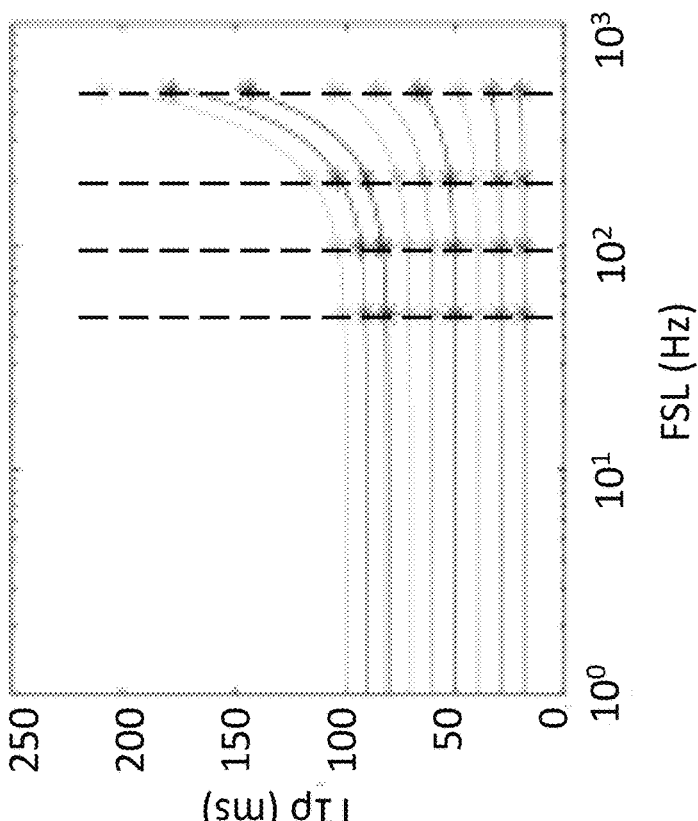

Similarly, FIG. 4 illustrates the measured $T_{1\rho}$ and $R_{1\rho}$, where $R_{1\rho}=1/T_{1\rho}$, in regions of interest (ROIs) of the retrospectively MRF-derived maps illustrated in FIG. 3 as compared to the ground truth dispersion curve (solid lines). The FSL frequencies of each of the maps of FIS. 3 (50, 100, 200, and 500 Hz) are marked by the vertical dashed lines on the graphs of FIG. 4, and the ground truth is indicated by the solid lines.

Figure 5:
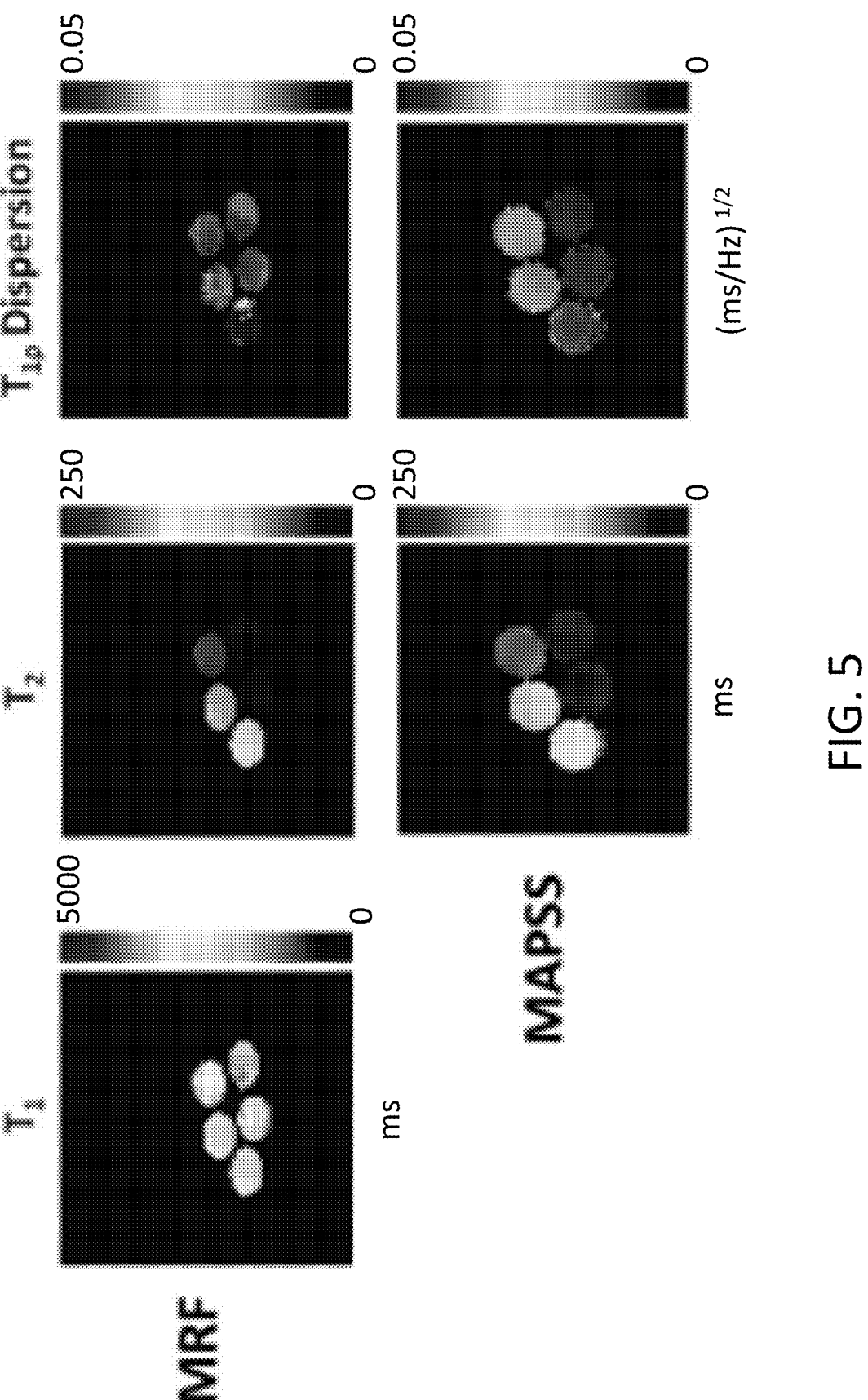
FIG. 5 illustrates MRF estimated $T_1$, $T_2$, and $T_{1\rho}$ dispersion maps as well as MAPSS $T_2$ and $T_{1\rho}$ dispersion maps for an agarose and glucose phantom.

FIG. 5 further illustrates differences observed in $T_2$ and $T_{1\rho}$ dispersion maps for the agarose and glucose phantom for the MRF technique and for the MAPSS technique. As illustrated, minimal differences are observed between MRF and MAPSS particularly with respect to in $T_{1\rho}$ dispersion.

Simply, FIGS. 2-5 illustrate strong agreement between the MRF technique described herein and ground truth references and the MAPSS technique for all of $T_1$, $T_2$, and $T_{1\rho}$. To the extent errors were present, they tended to be greater for high dispersion values for both simulation and physical phantoms. Herein, while the various maps illustrated in FIGS. 2-5 are shown in grayscale/black-and-white, they may be represented in color.

Considering this, the feasibility of direct characterization of $T_{1\rho}$ dispersion by MRF is possible according to the technique described herein. This is supported by simulations showing strong agreement between ground truth and MRF estimated parameters. With phantoms, there is generally good agreement between $T_{1\rho}$ dispersion maps derived from conventional $T_{1\rho}$ mapping and $T_{1\rho}$ dispersion generated by the MRF technique described herein.

Moreover, $T_{1\rho}$ dispersion via MRF can significantly reduce the required acquisition time and radiofrequency pulse energy deposition or amplifier requirements as compared to conventional $T_{1\rho}$ dispersion collection methods due to the acquisition of MR signal data at a single fixed FSL rather than different spin-lock frequencies. The MRF $T_{1\rho}$ dispersion technique herein further has the benefit of providing $T_1$ and $T_2$ maps in addition to the $T_{1\rho}$ dispersion model parameters. Thus, $T_{1\rho}$ dispersion acquisition may be achieved with a greater range of applications and system hardware.

Any aspect of the above disclosure may be implemented by a process of an MRI system, or by a processor of a separate computing device(s). It is further noted than any aspect may be executed locally (e.g., at the site of the MRI system or of the MRI imaging), or remotely. For example, MR data acquisition may be performed locally to the MRI system at a hospital or like clinical location, while other aspects of the present disclosure are performed at a remote central processing location and at a different time than the data acquisition. Still further, it is noted that the various aspects of the present disclosure may be distributed across any number of processors and/or computing systems.

While various features are presented above, it should be understood that the features may be used singly or in any combination thereof. Further, it should be understood that variations and modifications may occur to those skilled in the art to which the claimed examples pertain.

What is claimed is:

1. A magnetic resonance fingerprinting (MRF) method, comprising:

applying an MRF pulse sequence to tissue of a subject;

acquiring magnetic resonance (MR) signal data as a result of the application of the MRF pulse sequence;

comparing the MR signal data to a predefined MRF dictionary, the MRF dictionary comprising a model of $T_{1\rho}$ dispersion; and determining a property of the tissue from the $T_{1\rho}$ dispersion model based on a result of the comparison, wherein the MRF pulse sequence includes a single fixed spin-lock frequency.

2. The method according to claim 1, wherein $T_{1\rho}$ dispersion is modeled according to:

$$T_{1\rho}(\omega) = \frac{\left(q^2 D\right)^2 + \omega^2}{\gamma^2 g^2 D} = m^2 \left(q^2 D\right)^2 + m^2 \omega^2$$

where $$T_{1\rho}(0) = m^2 \left(q^2 D\right)^2 = T_2 \text{ and } T_{1\rho}(\omega) = T_2 + (m\omega)^2$$

where $\gamma$ is a hydrogen gyromagnetic ratio, D is a self-diffusion coefficient, q is a spatial frequency of a local magnetic field variation, g is a mean local magnetic gradient strength, $\omega$ is frequency, and m is a mediation coefficient that mediates a strength of a $T_{1\rho}$ dispersion effect and represents a combination of $\gamma$, D, and g.

3. The method according to claim 1, wherein $T_{1\rho}$ dispersion is modeled according to:

$$T_{1\rho}(\omega) = T_2 + m\omega$$

where $\omega$ is frequency, and m is a mediation coefficient that mediates a strength of a $T_{1\rho}$ dispersion effect and represents a combination of a hydrogen gyromagnetic ratio, a self-diffusion coefficient, and a mean local magnetic gradient strength.

4. The method according to claim 1, wherein the determined tissue property relates to tissue degeneration.

5. The method according to claim 1, further comprising:

identifying an osteoarthritis or muscle degeneration condition in the subject based on the identified property.

6. The method of claim 1, further comprising:

applying a plurality MRF pulse sequencies; and tracking a change in $T_{1\rho}$ dispersion of the tissue of the subject over the plurality of applied MRF sequences.

7. The method of claim 1, further comprising:

applying a plurality MRF pulse sequencies; and tracking a change in the determined tissue property over the plurality of applied MRF sequences.

8. The method according to claim 1, further comprising:

determining a $T_{1\rho}$ dispersion by retrospectively determining $T_{1\rho}$ at a plurality of spin-lock frequencies based on the model of the MRF dictionary.

9. The method according to claim 1, wherein the MRF dictionary comprises fingerprints of at least $T_1$, $T_2$, and a mediation coefficient that mediates a strength of a $T_{1\rho}$ dispersion effect.

10. The method according to claim 1, wherein the MR signal data is compared to the predefined MRF dictionary with a machine learning system trained to identify MR properties of the MRF dictionary based on input MR signal data.

11. A magnetic resonance fingerprinting (MRF) method, comprising:

applying an MRF pulse sequence to tissue of a subject;

acquiring magnetic resonance (MR) signal data as a result of the application of the MRF pulse sequence;

comparing the MR signal data to a predefined MRF dictionary, the MRF dictionary comprising a model of $T_{1\rho}$ dispersion; and determining a property of the tissue from the $T_{1\rho}$ dispersion model based on a result of the comparison, wherein $T_{1\rho}$ dispersion is modeled according to:

$$T_{1\rho}(\omega) = \frac{\left(q^2 D\right)^2 + \omega^2}{\gamma^2 g^2 D} = m^2 \left(q^2 D\right)^2 + m^2 \omega^2$$

where $$T_{1\rho}(0) = m^2 \left(q^2 D\right)^2 = T_2 \text{ and } T_{1\rho}(\omega) = T_2 + (m\omega)^2$$

where $\gamma$ is a hydrogen gyromagnetic ratio, D is a self-diffusion coefficient, q is a spatial frequency of a local magnetic field variation, g is a mean local magnetic gradient strength, $\omega$ is frequency, and m is a mediation coefficient that mediates a strength of a $T_{1\rho}$ dispersion effect and represents a combination of $\gamma$, D, and g.

12. The method according to claim 11, wherein the determined tissue property relates to tissue degeneration.

13. The method according to claim 11, further comprising:

identifying an osteoarthritis or muscle degeneration condition in the subject based on the identified property.

14. The method of claim 11, further comprising:

applying a plurality MRF pulse sequencies; and tracking a change in $T_{1\rho}$ dispersion of the tissue of the subject, or in the determined tissue property, over the plurality of applied MRF sequences.

15. The method according to claim 11, wherein the MRF dictionary comprises fingerprints of at least $T_1$, $T_2$, and m.

16. A magnetic resonance fingerprinting (MRF) method, comprising:

applying an MRF pulse sequence to tissue of a subject;

acquiring magnetic resonance (MR) signal data as a result of the application of the MRF pulse sequence;

comparing the MR signal data to a predefined MRF dictionary, the MRF dictionary comprising a model of $T_{1\rho}$ dispersion; and determining a property of the tissue from the $T_{1\rho}$ dispersion model based on a result of the comparison, wherein $T_{1\rho}$ dispersion is modeled according to:

$$T_{1\rho}(\omega) = T_2 + m\omega$$

where $\omega$ is frequency, and m is a mediation coefficient that mediates a strength of a $T_{1\rho}$ dispersion effect and represents a combination of a hydrogen gyromagnetic ratio, a self-diffusion coefficient, and a mean local magnetic gradient strength.

17. The method according to claim 16, wherein the determined tissue property relates to tissue degeneration.

18. The method according to claim 16, further comprising:

identifying an osteoarthritis or muscle degeneration condition in the subject based on the identified property.

19. The method of claim 16, further comprising:

applying a plurality MRF pulse sequencies; and tracking a change in $T_{1\rho}$ dispersion of the tissue of the subject, or in the determined tissue property, over the plurality of applied MRF sequences.

20. The method according to claim 16, wherein the MRF dictionary comprises fingerprints of at least $T_1$, $T_2$, and m.

\* \* \* \* \*